US00PP31976P2

(12) United States Plant Patent
Smith

(10) Patent No.: US PP31,976 P2
(45) Date of Patent: Jul. 14, 2020

(54) ***CHRYSANTHEMUM* PLANT NAMED 'CIFZ0069'**

(50) Latin Name: ***Chrysanthemum* x *morifolium***
Varietal Denomination: CIFZ0069

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/350,950

(22) Filed: Feb. 4, 2019

(51) Int. Cl.
*A01H 5/02* (2018.01)
*A01H 6/14* (2018.01)

(52) U.S. Cl.
USPC ..... Plt./296
CPC ..... *A01H 6/1424* (2018.05)

(58) Field of Classification Search
USPC ..... Plt./296
CPC ..... A01H 6/1424; A01H 5/02
See application file for complete search history.

*Primary Examiner* — Keith O. Robinson
(74) *Attorney, Agent, or Firm* — Dale Skalla

(57) ABSTRACT

A new garden type *Chrysanthemum* plant named 'CIFZ0069' particularly distinguished by the medium size plant with a round mound plant habit, a small sized (1.5 inch) flower, red-bronze decorative flower color and a natural season response in late September to mid-October

1 Drawing Sheet

Latin name of the genus and species of the plant claimed: *Chrysanthemum* x *morifolium*.

Varietal denomination: 'CIFZ0069'.

BACKGROUND OF THE NEW PLANT

The present invention comprises a new *Chrysanthemum*, botanically known as *Chrysanthemum* x *morifolium*, and hereinafter referred to by the variety name 'CIFZ0069'.

'CIFZ0069' is a product of a planned breeding program. The new cultivar is a medium size plant with round mound plant habit, a small sized (1.5 inch) flower, red-bronze decorative flower color and a natural season response in late September to mid-October.

'CIFZ0069' originated from 'CIFZ0031', a stock x-rayed at 1750 RAD in December of 2015 in Gilroy, Calif. 'CIFZ0069' was selected from the resulting population on Mar. 8, 2016 in Gilroy, Calif.

The female parent was the variety 'CIFZ0031', U.S. Pat. No. 23,924.

When compared to the female parent, 'CIFZ0069' is/has:

a similar flower type with a bit smaller flower size but darker bronze/almost red flower color versus orange of 'CIFZ0031'.
a couple days slower in blackcloth response and natural season response than 'CIFZ0031'.
has a similar plant habit and similar or a bit smaller overall plant size than 'CIFZ0031'.

As 'CIFZ0069' is a mutant plant, there is no male parent.

The first act of asexual reproduction of 'CIFZ0069' was accomplished when vegetative stem cuttings were propagated from the initial selection in April 2016 in Gilroy, Calif.

BRIEF SUMMARY OF INVENTION

Horticultural examination of plants grown from cuttings of the plant initiated in April 2016 and continuing thereafter, has demonstrated that the combination of characteristics as herein disclosed for 'CIFZ0069' are firmly fixed and are retained through successive generations of asexual reproduction.

'CIFZ0069' has not been observed under all possible environmental conditions. The phenotype may vary significantly with variations in environment such as temperature, light intensity and day length.

A Plant Breeder's Right for this cultivar has not yet been applied for. 'CIFZ0069' has not been made publicly available prior to the effective filing date of this application, notwithstanding any disclosure that may have been made less than one year prior to the effective filing date of this application by the inventor or another who obtained 'CIFZ0069' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0069' with colors being as true as possible with an illustration of this type.

Figure 1:
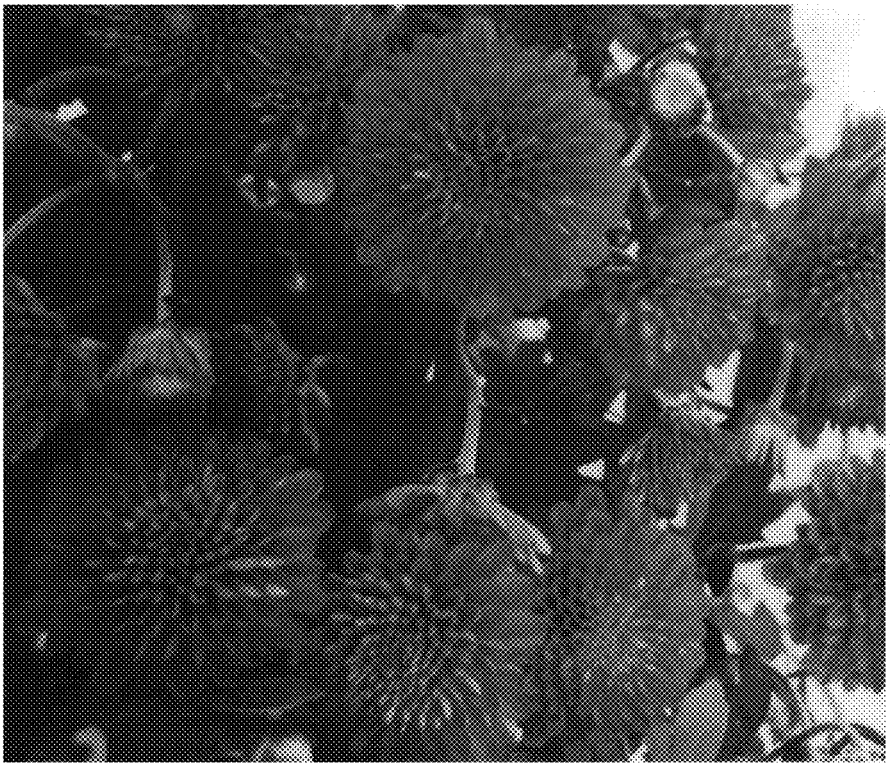
Figure 2:
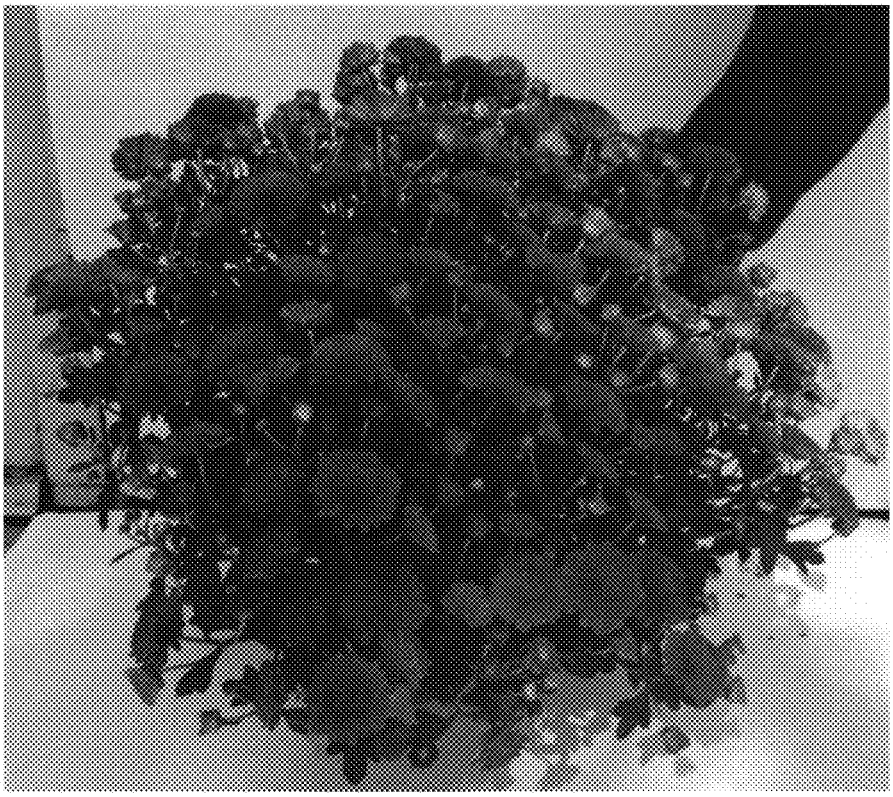

The photographic drawings show in FIG. 1 a close view of flower of the new variety and in FIG. 2 a flowering plant from an outdoor trial.

The aforementioned photographs: FIG. 1, as well as FIG. 2, were taken in August 2018 both showing a plant from the same blackcloth indoor trial in Gilroy, Calif.

These plants were about 10 weeks of age. One rooted cutting per pot had been planted in a one gallon pot, not pinched in week 24, and black clothed from week 25. Plants started flowering in August.

DETAILED BOTANICAL DESCRIPTION

The measurements were taken in Gilroy, Calif. in August 2018 on the plants from the aforementioned trial.

Color references are made to The Royal Horticultural Society Colour Chart (R.H.S.) 2015.

TABLE 1

DIFFERENCES BETWEEN THE NEW VARIETY 'CIFZ0069' AND TWO MOST SIMILAR VARIETIES:

| | 'CIFZ0069' | 'CIFZ0048', U.S. Plant Pat. No. 29,639 |
|---|---|---|
| Flowering response (blackcloth): | Similar | Similar |
| Flowering response (natural): | Similar | Similar |
| Flower color: | Similar | Similar |
| Flower size: | Larger | Smaller |
| Flowering: | Not flowering uniform | Flowering very uniform |
| Plant habit: | Wider | More upright |

| | 'CIFZ0069' | 'Pavia Red', PP23,134 |
|---|---|---|
| Flowering response (blackcloth): | 2 weeks faster | 2 weeks later |
| Flowering response (natural): | Similar | Similar |
| Flower size: | Similar | Similar |
| Plant habit: | Less round/more mound | Very round |
| Flower longevity | Long lasting | Shorter lasting |
| Plant size: | Smaller | Bigger |

Plant:

*Form, growth and habit.*—Herbaceous garden-type, stems upright and outwardly spreading, freely branching, strong and moderately vigorous growth habit.

*Plant height* (*above soil*).—11-16 cm.

*Plant height* (*inflorescence included*).—17-29 cm.

*Plant width.*—33-35 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 139A.

*Immature leaf, color lower surface.*—RHS 137C.

*Mature leaf, color, upper surface.*—RHS 137A.

*Mature leaf, color lower surface.*—RHS NN137C.

*Length.*—5.6 cm.

*Width.*—4.7-5.2 cm.

*Shape.*—Ovate, with distinct lobes.

*Base shape.*—Attenuate.

*Apex shape.*—Mucronate.

*Margin.*—5-lobed (palmate), edge dentate.

*Texture, upper surface.*—Bifid hairs.

*Texture, lower surface.*—Bifid hairs.

*Color of veins, upper surface.*—RHS 138B.

*Color of veins, lower surface.*—RHS N137A.

*Pattern of veining.*—Palmate.

*Petiole color.*—RHS 138A.

*Petiole Length.*—1.8-2.2 cm.

*Diameter.*—0.2-0.3 cm.

*Texture.*—Covered with bifid hairs.

Stem:

*Quantity of main branches per plant.*—5-8.

*Color of stem.*—RHS 138A.

*Length of stem.*—7-9 cm.

*Diameter.*—0.6 cm.

*Length of internodes.*—1.0-1.6 cm.

*Texture.*—Bifid hairs.

*Color of peduncle.*—RHS 138B.

*Length of peduncle.*—6.7-7.8 cm.

*Peduncle diameter.*—0.3 cm.

*Texture.*—Bifid hairs.

Inflorescence:

*Type.*—Compositae, solitary, decorative type inflorescences borne terminally above foliage, ligulate ray florets florets arranged on a capitulum.

*Quantity of short days to flowering* (*response time*).—Approximately 5.5 weeks.

*Natural season flowering.*—Late September to mid-October.

*Quantity of inflorescences per plant.*—130-140.

*Lastingness of individual blooms on the plant.*—More than six weeks from first color.

*Fragrance.*—Slightly spicy.

Bud (when showing color):

*Color.*—RHS 46A.

*Length.*—0.6-0.8 cm.

*Width.*—1.4 cm.

*Shape.*—Oblate.

Immature inflorescence:

*Diameter.*—3.4 cm.

*Color of ray florets, upper surface.*—RHS 46A.

*Color of ray florets, lower surface.*—RHS 46A overlain with RHS 7A.

Mature inflorescence:

*Diameter.*—4.3 cm.

*Depth.*—1.6 cm.

*Total diameter of disc.*—No disc.

*Receptacle color.*—RHS 141B.

*Receptacle height.*—0.5 cm.

*Receptacle diameter.*—0.3 cm.

Ray florets:

*Average quantity of florets.*—Between 230 and 240 in many whorls.

*Color of florets, upper surface* (*abaxial*).—RHS 46A.

*Color inner surface* (*adaxial*).—RHS 46A overlain with RHS 7A.

*Length.*—1.9-2.1 cm.

*Width/diameter.*—0.5 cm.

*Shape.*—Elliptical.

*Apex shape.*—Most obtuse and dentate.

*Base shape.*—Tube.

*Margin.*—Entire, small incisions may occur at the tip.

*Texture, upper surface.*—Papillate.

*Lower surface.*—Papillate.

Disc florets: None present.

Phyllaries:

*Quantity.*—20-30.

*Color, upper surface.*—RHS 137B.

*Color, lower surface.*—RHS 137C.

*Length.*—0.6 cm.

*Width.*—0.3 cm.

*Shape.*—Lanceolate.

*Apex shape.*—Acute.

*Base.*—Fused.

*Margins.*—Entire.

*Texture, upper surface*.—Glabrous.
*Texture, lower surface*.—Canescent.

Reproductive organs:
*Pistil*.—One.
*Length*.—0.4-0.5 cm.
*Style color*.—RHS 150A.
*Style length*.—0.2-0.3 cm.
*Stigma color*.—RHS 7D.
*Stigma shape*.—Bi-parted.
*Ovary color*.—RHS 145C.
*Ovary length*.—0.15-0.2 cm.
*Ovary width*.—0.1 cm.

Androecium:
*Stamens*.—None (are normally present in disk florets, these are not developed).
*Fertility/seed set*.—Has not been determined to date.
*Disease/pest resistance*.—Has not been determined to date.

What is claimed is:

1. A new and distinct variety of *Chrysanthemum* plant named 'CIFZ0069' substantially as illustrated and described herein.

* * * * *